United States Patent
Romer et al.

(10) Patent No.: US 9,441,055 B1
(45) Date of Patent: Sep. 13, 2016

(54) ARYLCYCLOBUTENES

(71) Applicants: Dow Global Technologies LLC, Midland, MI (US); Rohm and Haas Electronic Materials LLC, Marlborough, MA (US); Rohm and Haas Company, Philadelphia, PA (US)

(72) Inventors: Duane R. Romer, Midland, MI (US); Matthew M. Yonkey, Sanford, MI (US); Michael K. Gallagher, Hopkinton, MA (US); Kevin Y. Wang, Marlborough, MA (US); Xiang Qian Liu, Collegeville, PA (US); Raymond J. Thibault, Wrentham, MA (US); Kim S. Ho, Washington Crossing, PA (US); Gregory D. Prokopowicz, Worcester, MA (US); Corey O'Connor, Oakham, MA (US); Elissei Iagodkine, Marlborough, MA (US); Robert K. Barr, Shrewsbury, MA (US)

(73) Assignees: Dow Global Technologies LLC, Midland, MI (US); Rohm and Haas Electronic Materials LLC, Marlborough, MA (US); Rohm and Haas Company, Philadelphia, PA (US)

( * ) Notice: Subject to any disclaimer, the term of this patent is extended or adjusted under 35 U.S.C. 154(b) by 0 days.

(21) Appl. No.: 14/858,224

(22) Filed: Sep. 18, 2015

(51) Int. Cl.
| | |
|---|---|
| *C08F 20/28* | (2006.01) |
| *C07C 69/618* | (2006.01) |
| *C07C 233/22* | (2006.01) |
| *C08F 22/26* | (2006.01) |
| *C07C 43/178* | (2006.01) |
| *C08F 22/20* | (2006.01) |
| *C08F 16/32* | (2006.01) |
| *C08F 22/38* | (2006.01) |
| *C09D 133/14* | (2006.01) |
| *C09D 135/02* | (2006.01) |
| *C09D 135/00* | (2006.01) |
| *C09D 129/10* | (2006.01) |
| *B05D 7/26* | (2006.01) |

(52) U.S. Cl.
CPC ............ *C08F 20/28* (2013.01); *B05D 7/26* (2013.01); *C07C 43/1788* (2013.01); *C07C 69/618* (2013.01); *C07C 233/22* (2013.01); *C08F 16/32* (2013.01); *C08F 22/20* (2013.01); *C08F 22/26* (2013.01); *C08F 22/38* (2013.01); *C09D 129/10* (2013.01); *C09D 133/14* (2013.01); *C09D 135/00* (2013.01); *C09D 135/02* (2013.01); *C07C 2102/06* (2013.01)

(58) Field of Classification Search
None
See application file for complete search history.

(56) References Cited

U.S. PATENT DOCUMENTS

| | | | | |
|---|---|---|---|---|
| 5,026,892 | A * | 6/1991 | Kirchhoff | C07C 13/44 556/419 |
| 6,083,661 | A * | 7/2000 | Oaks | C07C 247/16 430/194 |
| 2004/0063883 | A1 * | 4/2004 | Hayashi | C08G 61/12 526/279 |
| 2004/0148766 | A1 * | 8/2004 | Noguchi | H05K 3/4655 29/830 |

FOREIGN PATENT DOCUMENTS

| | | | |
|---|---|---|---|
| JP | 2005062405 | A * | 3/2005 |
| JP | 4277616 | B2 | 6/2009 |
| JP | 4281460 | B2 | 6/2009 |
| JP | 4289070 | B2 | 7/2009 |
| JP | 4341337 | B2 | 10/2009 |

OTHER PUBLICATIONS

JP 2005062405 A, Mar. 2005, English translation.*

* cited by examiner

*Primary Examiner* — Satya Sastri
(74) *Attorney, Agent, or Firm* — S. Matthew Cairns

(57) ABSTRACT

Arylclobutene-containing multi-functional monomers are useful in the preparation of arylcyclobutene-based polymer coatings. Compositions comprising one or more arylclobutene-containing multi-functional monomers and one or more oligomers comprising as polymerized units one or more arylcyclobutene monomer provide arylcyclobutene-based polymer coatings having reduced stress. Such compositions are useful in the manufacture of electronic devices.

13 Claims, No Drawings

ARYLCYCLOBUTENES

The present invention relates generally to the field of dielectric materials and more particularly to dielectrics for use in electronic device manufacture.

Current trends for smaller, higher performing electronic devices are pushing the demand for thinner wafers used in the manufacture of these devices. Thinner wafers provide advantages in heat dissipation and in increased interconnect (such as through silicon vias) density for 3D integration. However, thinner wafers are more subject to deformation due to stresses, as evidenced by wafer bow and/or warpage. Wafer bow is defined as the deviation of the center point of the median surface of a free, un-clamped wafer from the median surface to the reference plane which is defined by the three corners of an equilateral triangle. Wafer warpage is defined as the difference between the maximum and minimum distances of the median surface of a free, un-clamped wafer from the reference plane which is also defined by the three corners of an equilateral triangle.

Polymer-based permanent dielectrics are widely used in the manufacture of electronic devices. Typically, such polymer-based dielectrics are coated on a wafer, such as by spin-coating, and then cured. The tendency for a polymer-based coating to shrink during cure imparts stress to the wafer which can manifest as wafer bow. As wafer diameters get larger and wafer thicknesses get thinner, the problem of wafer bow is exacerbated to the point of causing difficulties with wafer handling.

Arylcyclobutene-based polymers are used as permanent dielectric materials in a variety of electronic applications, such as microelectronic packaging and interconnect applications. Conventionally, arylcyclobutene-based polymers are prepared from the polymerization of bis-arylcbutene monomers, that is, monomers containing two arylcyclobutene moieties. Certain bis-arylcyclobutene monomers are disclosed in U.S. Pat. Nos. 4,812,588 and 5,026,892, and in Japanese Pat. No. 4282460B. Arylcyclobutene-based polymers possess many desirable properties for electronic applications. However, conventional arylcyclobutene-based polymers inherently have a relatively high stress and can impart undesirable wafer bow when coated on relatively thin (such as <200 µm thick) wafers. For example, photoimageable, aqueous developable arylcyclobutene-based materials typically contain an epoxy-based crosslinker to prevent unexposed film thickness loss (UTFL) during the development step. While such epoxy-based crosslinkers are effective to reduce or prevent unwanted UTFL, the resulting epoxy-crosslinked arylcyclobutene polymers typically have increased residual stress as compared to the uncrosslinked polymer, resulting in unacceptable wafer bow. Accordingly, there remains a need for arylcyclobutene-based polymer coatings, particularly photoimageable arylcyclobutene-based coatings, that have reduced stress and provide reduced wafer bow when coated on relatively thin wafers.

The present invention provides a compound of the formula (1)

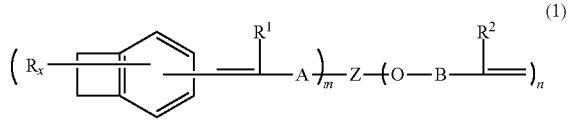

(1)

wherein each A is independently chosen from $-CR^3R^4-$, $-O-$, $-C(=O)O-$, and $-C(=O)NH-$; each B is independently chosen from $-CR^3R^4-$ and $-C(=O)-$; each R is independently chosen from halo, cyano, hydroxy, carboxy, $C_{1-6}$ alkoxy, $C_{1-6}$ alkyl, $C_{1-6}$ haloalkyl, $C_{2-6}$ alkenyl, carboxy $C_{1-6}$ alkyl, $-(C=O)-C_{1-6}$ alkyl, $-G-(C=O)-C_{1-6}$ alkyl, $-(C=O)-G-C_{1-6}$ alkyl, $-O-C_{4-20}$ aryl, $-(C=O)-C_{4-20}$ aryl, $-G-(C=O)-C_{4-20}$ aryl, and $-(C=O)-G-C_{4-20}$ aryl; each of $R^1$, $R^2$, $R^3$ and $R^4$ is independently chosen from H, $C_{1-10}$ alkyl, $C_{2-10}$ alkenyl, $C_{2-10}$ alkynyl, and $C_{4-15}$ aryl; Z is an organic radical having 2 to 50 carbon atoms; G is O or $N(R')_2$; each R' is independently chosen from H, $C_{1-6}$ alkyl, $C_{4-10}$ aryl, and $C_{7-15}$ aralkyl; x is the number of R groups and is an integer of from 0 to 2; m is an integer of from 1 to 6; n is an integer of from 0 to 5; and m+n=3 to 6.

Additionally, the present invention provides a polymer comprising as polymerized units one or more monomers of formula (1) described above.

Also provided by the present invention is a composition comprising: one or more compounds of the formula (1) described above; and one or more organic solvents.

The present invention further provides a crosslinkable composition comprising: one or more compounds of formula (1) described above; and one or more oligomers. Preferably, this crosslinkable composition further comprises one or more organic solvents or is in the form of a dry film.

Still further, the present invention provides a method of forming a film on a substrate comprising: providing a substrate; coating a layer of a composition comprising one or more compounds of the formula (1) described above and one or more organic solvents on a surface of the substrate; and curing the coating.

As used throughout this specification, the following abbreviations shall have the following meanings, unless the context clearly indicates otherwise: ° C.=degree Celsius; min.=minutes; hr.=hours; g=gram; L=liter; µm=micron=micrometer; nm=nanometer; mm=millimeter; mL=milliliter; MPa=megapascal; $M_w$=weight average molecular weight; and $M_n$=number average molecular weight. "Wt %" refers to percent by weight, based on the total weight of a referenced composition, unless otherwise noted.

The term "alkyl" includes linear, branched and cyclic alkyl. Likewise, "alkenyl" refers to linear, branched and cyclic alkenyl. "Aryl" refers to aromatic carbocycles and aromatic heterocycles. As used herein, the term "aliphatic" refers to an open-chain carbon- containing moiety, such as alkyl, alkenyl and alkynyl moieties, which may be linear or branched. Also as used herein, the term "alicyclic" refers to a cyclic aliphatic moiety, such as cycloalkyl and cycloalkenyl. Such alicyclic moieties are non-aromatic, but may include one or more carbon-carbon double bonds. "Halo" refers to fluoro, chloro, bromo, and iodo. The term "(meth)acrylate" refers to both methacrylate and acrylate, and likewise the term (meth)acrylamide refers to both methacrylamide and acrylamide. By the term "curing" is meant any process, such as polymerization or condensation, that increases the molecular weight of a material or composition. "Curable" refers to any material capable of being cured under certain conditions. The term "polymer" also includes oligomers. The term "oligomer" refers to relatively low molecular weight materials such as dimers, trimers, tetramers, pentamers, hexamers, and the like that are capable of further curing. The articles "a", "an" and "the" refer to the singular and the plural. All amounts are percent by weight and all ratios are molar ratios, unless otherwise noted. All numerical ranges are inclusive of the endpoints and combinable in any order, except where it is clear that such numerical ranges are constrained to add up to 100%.

The inventors have found certain compounds useful as monomers for the formation of arylcyclobutene-based polymers that have reduced residual stress as compared to conventional arylcyclobutene-based polymers. The present monomers comprise three or more, such as three to six, reactive moieties chosen from vinyl-substituted arylcyclobutene moieties, allyl ether moieties, (meth)acrylate moieties and (meth)acrylamide moieties, wherein at least one vinyl-substituted arylcyclobutene moiety is present. In the present compounds, each arylcyclobutene moiety is directly bonded to the terminal ethylenically unsaturated carbon of an allyl ether moiety, a vinyl ester moiety, or a vinyl amide moiety, and wherein the allyl ether oxygen or the non-carbonyl oxygen of the vinyl ester moiety or vinyl amide moiety are directly bonded to an organic radical having sufficient flexibility to reduce the residual stress of a cured polymer coating as relative to a cured conventional arylcyclobutene-based polymer coating. Preferably, the arylcyclobutene moieties are benzocyclobutene moieties or substituted benzocyclobutene moieties.

The monomers of the present invention are compounds of formula (1)

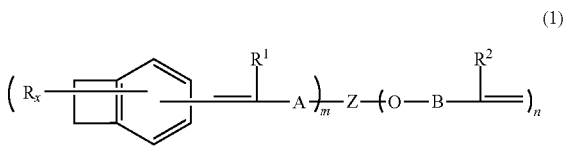

(1)

wherein each A is independently chosen from —$CR^3R^4$—O—, —C(=O)O—, and —C(=O)NH—; each B is independently chosen from —$CR^3R^4$— and —C(=O)—; each R is independently chosen from halo, cyano, hydroxy, carboxy, $C_{1-6}$ alkoxy, $C_{1-6}$ alkyl, $C_{1-6}$ haloalkyl, $C_{2-6}$ alkenyl, carboxy $C_{1-6}$ alkyl, —(C=O)—$C_{1-6}$ alkyl, —G—(C=O)—$C_{1-6}$ alkyl, —(C=O)—G—$C_{1-6}$ alkyl, —O—$C_{4-20}$ aryl, —(C=O)—$C_{4-20}$ aryl, —G—(C=O)—$C_{4-20}$ aryl, and —(C=O)—G—$C_{4-20}$ aryl; each of $R^1$, $R^2$, $R^3$ and $R^4$ is independently chosen from H, $C_{1-10}$ alkyl, $C_{2-10}$ alkenyl, $C_{2-10}$ alkynyl, and $C_{4-15}$ aryl; Z is an organic radical having 2 to 50 carbon atoms; G is O or $N(R')_2$; each R' is independently chosen from H, $C_{1-6}$ alkyl, $C_{4-10}$ aryl, and $C_{7-15}$ aralkyl; x is the number of R groups and is an integer of from 0 to 2; m is an integer of from 1 to 6; n is an integer of from 0 to 5; and m+n=3 to 6. Preferably, A is —$CR^3R^4$—O— or —C(=O)O—, and more preferably A is —C(=O)O—. More preferably, each A is the same, and yet more preferably each A is —C(=O)O—. B is preferably —$CR^3R^4$—. More preferably, each B is the same, and yet more preferably each B is —$CR^3R^4$—. Each R is preferably independently chosen from halo, cyano, hydroxy, carboxy, $C_{1-6}$ alkoxy, $C_{1-6}$ alkyl, $C_{1-6}$ haloalkyl, $C_{2-6}$ alkenyl, carboxy $C_{1-6}$ alkyl, —(C=O)—$C_{1-6}$ alkyl, —G—(C=O)—$C_{1-6}$ alkyl, —(C=O)—G—$C_{1-6}$ alkyl, —O—$C_{4-20}$ aryl, —(C=O)—$C_{6-20}$ aryl, —G—(C=O)—$C_{6-20}$ aryl, and —(C=O)—G—$C_{6-20}$ aryl, more preferably from halo, hydroxy, carboxy, $C_{1-6}$ alkoxy, $C_{1-6}$ alkyl, $C_{1-6}$ haloalkyl, carboxy $C_{1-6}$ alkyl, —O—$C_{6-20}$ aryl, —(C=O)—$C_{6-20}$ aryl, —G—(C=O)—$C_{6-20}$ aryl, and —(C=O)—G—$C_{6-20}$ aryl, yet more preferably from halo, carboxy, $C_{1-6}$ alkoxy, $C_{1-6}$ alkyl, $C_{1-3}$ haloalkyl, carboxy $C_{1-3}$ alkyl, —O—$C_{6-20}$ aryl, —(C=O)—$C_{6-20}$ aryl, —O—(C=O)—$C_{6-20}$ aryl, and —(C=O)—O—$C_{6-20}$ aryl, and still more preferably from halo, $C_{1-3}$ alkoxy, $C_{1-3}$ alkyl, and $C_{1-3}$ haloalkyl. Each of $R^1$, $R^2$, $R^3$ and $R^4$ is preferably independently chosen from H, $C_{1-10}$ alkyl, $C_{2-10}$ alkenyl, $C_{2-10}$ alkynyl, and $C_{6-15}$ aryl. It is preferred that each $R^1$ and $R^2$ is independently chosen from H, $C_{1-10}$ alkyl, and $C_{2-10}$ alkenyl, more preferably from H, $C_{1-8}$ alkyl, and $C_{2-8}$ alkenyl, even more preferably from H and $C_{1-4}$ alkyl, and yet more preferably each $R^1$ and $R^2$ is H or methyl. It is preferred that each $R^3$ and $R^4$ is independently chosen from H, $C_{1-10}$ alkyl, and $C_{2-10}$ alkenyl, more preferably from H, $C_{1-8}$ alkyl, and $C_{2-8}$ alkenyl, and even more preferably from H and $C_{1-4}$ alkyl. More preferably, $R^3$ and $R^4$ are the same and even more preferably each $R^3$ and $R^4$ is H. When A=—C(=O)O—, it is preferred that $R^1$ is H or methyl, and more preferably $R^1$ is H. When A=—C(=O)NH—, it is preferred that $R^1$ is H. When B=—$CR^3R^4$—, it is preferred that $R^3$ and $R^4$ are both H. Z is preferably an organic radical having 3 to 50 carbon atoms, and more preferably from 4 to 45 carbon atoms. The organic radical of Z may have one or more ether linkages, one or more hydroxyl moieties, or a combination of one or more ether linkages and one or more hydroxyl moieties. The organic radical of Z is aliphatic, alicyclic or a combination thereof, and is preferably aliphatic. Preferably, the organic radical of Z is free of aryl moieties. G is preferably O. It is preferred that each R' is independently chosen from H, $C_{1-6}$ alkyl, $C_{6-10}$ aryl, and $C_{7-15}$ aralkyl, and more preferably from H, $C_{1-6}$ alkyl, and $C_{6-10}$ aryl. Preferably x=0 to 1, and more preferably x=0. It is preferred that m=1 to 4, more preferably m=1 to 3, and yet more preferably m=3. Preferably, n=0 to 4, more preferably n=0 to 3, and still more preferably n=0. It is preferred that m+n=3 to 5, and more preferably 3 or 4.

Exemplary groups for R in formula (1) include, without limitation, bromo, fluoro, cyano, hydroxy, methoxy, ethoxy, n-propoxy, iso-propoxy, n-butoxy, sec-butoxy, iso-butoxy, tert-butoxy, methyl, ethyl, n-propyl, iso-propyl, n-butyl, sec-butyl, iso-butyl, tert-butyl, n-pentyl, neo-pentyl, n-hexyl, 2-hexyl, 3-hexyl, trifluoromethyl, vinyl, allyl, but-2-ene-1-yl, carboxy, carboxy methyl, phenoxy, furyloxy, phenylcarbonyl, carbonyloxyphenyl, phenylamido, and diphenylamido. Preferred groups for R in formula (1) are bromo, fluoro, hydroxy, methoxy, ethoxy, n-propoxy, iso-propoxy, n-butoxy, sec-butoxy, iso-butoxy, tert-butoxy, methyl, ethyl, n-propyl, iso-propyl, n-butyl, sec-butyl, iso-butyl, tert-butyl, n-pentyl, neo-pentyl, n-hexyl, 2-hexyl, 3-hexyl, trifluoromethyl, and carboxy methyl. Exemplary groups for any of $R^1$, $R^2$, $R^3$ and $R^4$ in formula (1) include, but are not limited to, H, methyl, ethyl, n-propyl, iso-propyl, n-butyl, sec-butyl, iso-butyl, tert-butyl, n-pentyl, neo-pentyl, n-hexyl, 2-hexyl, 3-hexyl, vinyl, allyl, but-2-en-1-yl, furyl, phenyl, tolyl, xylyl, and naphthyl. Suitable groups for Z include, but are not limited to, $C_{2-30}$ alkylene, poly($C_{2-6}$ alkyleneoxy), $C_{3-30}$ hydroxyalkylene, $C_{3-30}$ polyhydroxyalkylene, alkoxylated $C_{3-30}$ hydroxyalkylene, alkoxylated $C_{3-30}$ polyhydroxyalkylene, and the like. As used herein, "alkoxylated" refers to reacting a moiety with an alkyleneoxide, such as ethyleneoxide, propyleneoxide or butyleneoxide. When an alkoxylated organic radical is used for Z, such organic radical may contain an average of from 1 to 10 alkyleneoxy moieties, and preferably contains an average of from 1 to 6 of such moieties.

Preferred monomers of formula (1) are those of formulae (2a) and (2b)

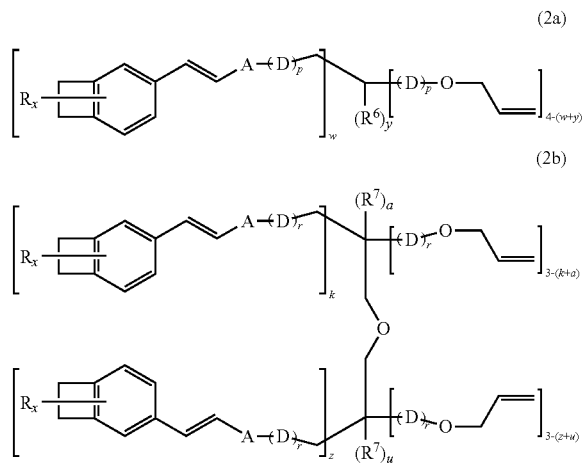

wherein A, R and x are as defined above for formula (1); each D is an alkyleneoxide residue having from 2 to 6 carbons; each $R^6$ is independently H, $C_{1-6}$ alkyl, $C_{1-6}$ hydroxyalkyl, or $-CH_2(D)_gOH$; each $R^7$ is independently H, $C_{1-6}$ alkyl, $C_{1-6}$ hydroxyalkyl, or $-CH_2(D)_gOH$; g represents an average number of repeat units and is an integer of from 0 to 10; p represents an average number of repeat units and is an integer of from 0 to 10; r represents an average number of repeat units and is an integer of from 0 to 10; w=1 to 4; y=0 or 1; a=0 to 2; k=1 to 3; z=0 to 3; u=0 to 3; a+u=0 to 3; k+z=1 to 6; k+(3−(k+a)+z+(3−(z+u)=3 to 6; and k+a+(3−(k+a)+z+u+(3−(z+u)=6. Preferably, D is an alkyleneoxide residue chosen from ethyleneoxide, propyleneoxide, and butyleneoxide. It is preferred that $R^6$ is H, $C_{1-4}$ alkyl, or $C_{1-4}$ hydroxy alkyl, and more preferably $R^6$ is $C_{1-4}$ alkyl, or $C_{1-4}$ hydroxy alkyl. It is preferred that $R^7$ is H, $C_{1-4}$ alkyl, or $C_{1-4}$ hydroxy alkyl, and more preferably $R^7$ is $C_{1-4}$ alkyl, or $C_{1-4}$ hydroxy alkyl. Preferably, p=0 to 8, and more preferably p=0 to 6. It will be appreciated by those skilled in the art that w+y=1 to 4. Preferably, r=0 to 8, and more preferably r=0 to 6. It is preferred that w=2 or 3, and more preferably 3. Preferably, k=2 or 3. It is preferred that z=1 to 3, and more preferably z=2 to 3. It is preferred that a is 0 or 1. Preferably, u=0 or 1. In one preferred embodiment of formula (2b), k+z=2 to 6, and more preferably 3 to 6. In another preferred embodiment of formula (2b), k=z=1. In another preferred embodiment of formula (2b), k=1 and z=0.

Preferred monomers of formulae (2a) and (2b) are those having the structures shown in formulae (3) to (19).

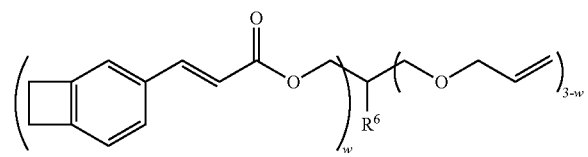

w = 1, $R^6$ = $CH_2-O-CH_2-CH=CH_2$ (3)
w = 1, $R^6$ = $CH_2CH_3$ (4)
w = 2, $R^6$ = $CH_2CH_3$ (5)

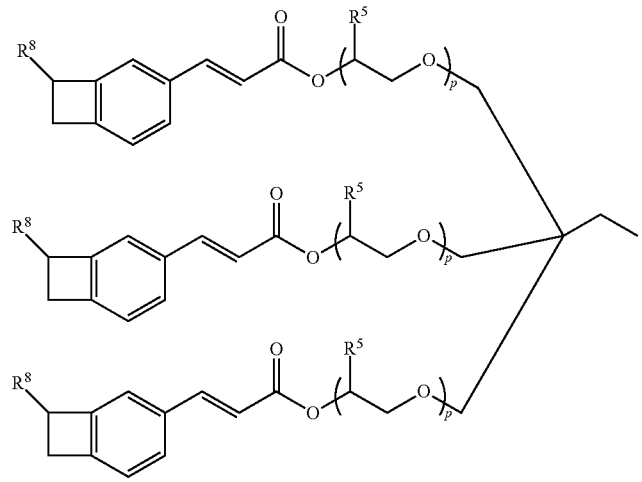

p = 1, $R^5$ = H, $R^8$ = H (6)
p = 2, $R^5$ = H, $R^8$ = H (7)
p = 5, $R^5$ = H, $R^8$ = H (8)
p = 2, $R^5$ = CH$_3$, $R^8$ = H (9)
p = 0, $R^8$ = H (10)
p = 3, $R^5$ = CH$_3$, $R^8$ = OCH$_3$ (11)

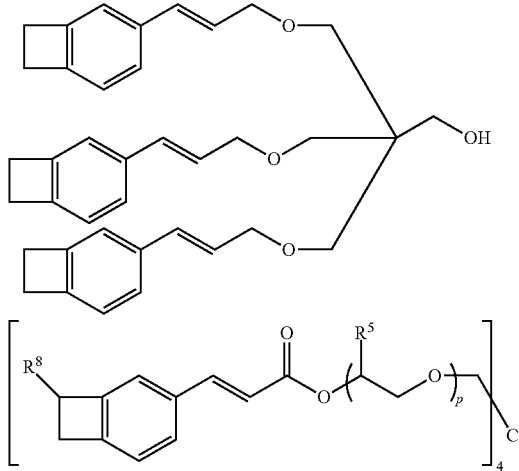

(12)

p = 0, $R^8$ = H (13)
p = 2, $R^5$ = CH$_3$, $R^8$ = H (14)
p = 5, $R^5$ = H, $R^8$ = H (15)
p = 3, $R^5$ = CH$_3$, $R^8$ = OCH$_3$ (16)

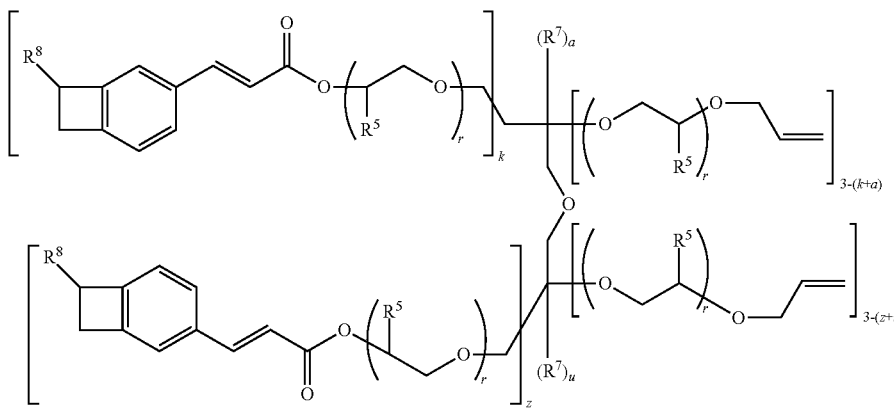

$R^8$ = H, r = 0, k = z = 2, a = u = 0 (17)
$R^8$ = OCH$_3$, $R^7$ = CH$_2$OH, r = 0, k = z = 2, a = u = 1 (18)
$R^8$ = H, $R^5$ = CH$_3$, r = 2, k = z = 3, a = u = 0 (19)

Monomers of the invention may be prepared by various methods known in the literature. For example, 3-bromobenzocyclobutene may be reacted with an organic radical having one or more terminal (meth)acrylate or allyl ether moieties via a Heck coupling reaction in the presence of a palladium (II) catalyst. Preferably, 3-bromobenzocyclobutene is reacted with timethylolpropane mono-, di- or tri—(meth)acrylate or timethylolpropane mono-, di- or tri-allyl ether, or an alkoxylated version thereof. The monomers are typically purified using conventional procedures before use to remove any remaining palladium catalyst and/or other impurities.

One or more monomers of the invention may be polymerized to form a homopolymer, or may be co-polymerized with a co-monomer to form a co-polymer. Suitable co-monomers are well-known in the art and are any that will polymerize with the benzocyclobutene moiety or any allyl ether moiety of the present compounds. In general, homopolymers are prepared by heating one or more of the present monomers, typically in a suitable solvent, to the polymerization initiation temperature of the particular monomer(s) used. While not wishing to be bound by theory, it is believed that these monomers homopolymerize by a Diels-Alder cycloaddition, so no catalyst initiator or curing agents are necessary for the polymerization to occur. Typically, polymerization of these monomers is initiated at a temperature of ≥150° C., and preferably ≥170° C., although lower or higher temperatures may be used depending upon the particular monomer(s) selected. The temperature at which the present monomers undergo polymerization is affected by any substituent on the cyclobutene ring. In general, when the cyclobutene ring is unsubstituted, the polymerization is initiated at ≥170° C. Electron-donating or electron-withdrawing substituents on the cyclobutene ring generally lower the polymerization initiation temperature. Suitable polymerization solvents are any organic solvents which dissolve the one or more monomers and have boiling points above the polymerization temperature of the monomers. Exemplary organic solvents include polar aprotic solvents such as amides and sulfones. Polymerization time is typically from 1 to 48 hours. For certain applications, it may be desired to stop the polymerization at the oligomer stage. Such oligomers composed of one or more monomers of the invention may be composed predominantly of dimers, trimmers, tetramers, and the like, and may then be subsequently further polymerized. As used herein, the terms "monomers of the invention" and "present monomers" are intended to include the individual compounds described herein, as well as dimers, trimmers and tetramers thereof which are then to be further polymerized. The polymers comprising one or more monomers of the invention can be used as is or can be isolated by adding a non-solvent, such as water or methanol, to precipitate the polymer from the solution and thereafter removing the organic solvent.

The monomers of the invention or oligomers thereof may be used as is or may be combined with any suitable organic solvent. Suitable organic solvents are those in which the present monomers are soluble. Particularly useful organic solvents for the present monomers are any solvents useful in the manufacture or formulation of arylcyclobutene oligomers. Exemplary organic solvents include, without limitation: aromatic hydrocarbons such as toluene, xylene, and mesitylene; alcohols such as 2-methyl-1-butanol, 4-methyl-2-pentanol, and methyl isobutyl carbinol; esters such as ethyl lactate, propylene glycol methyl ether acetate, methyl 2-hydroxyisobutyrate, methyl 3-methoxypropionate and 3-methoxy-1-butyl acetate; lactones such as gamma-butyrolactone; lactams such as N-methylpyrrolidinone; ethers such as propylene glycol methyl ether and dipropylene glycol dimethyl ether isomers (commercially available from The Dow Chemical Company as PROGLYDE™ DMM); ketones such as cyclohexanone and methylcyclohexanone; and mixtures thereof.

Also, the present monomers or oligomers thereof may be used as crosslinkers with a variety of polymers. Suitable crosslinkable compositions comprise one or more of the present monomers, one or more oligomers, optionally one or more organic solvents, and optionally one or more additives. Any of the organic solvents described above for the present monomer compositions may suitably be used in these crosslinkable compositions. Any oligomer that does not comprise as polymerized units a monomer of the invention and which reacts with the present monomers to form a crosslinked polymer may suitably be used in these compositions. It is preferred that the oligomer is an arylcyclobutene oligomer.

Arylcyclobutene oligomers useful in the present compositions are well-known in the art. Suitable arylcyclobutene oligomers include, but are not limited to, those having formula (20):

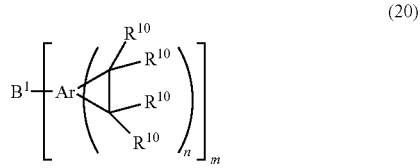

(20)

wherein $B^1$ is an n-valent linking group; Ar is a polyvalent aryl group and the carbon atoms of the cyclobutene ring are bonded to adjacent carbon atoms on the same aromatic ring of Ar; m is an integer of 1 or more; n is an integer of 1 or more; and each $R^{10}$ is a monovalent group. Preferably, the polyvalent aryl group, Ar, may be composed of 1 to 3 aromatic carbocyclic or heteroaromatic rings. It is preferred that the aryl group comprises a single aromatic ring, and more preferably a phenyl ring. The aryl group is optionally substituted with 1 to 3 groups chosen from $C_{1-6}$ alkyl, tri-$C_{1-6}$-alkylsilyl, $C_{1-6}$ alkoxy, halo, and carboxyl, preferably with one or more of $C_{1-3}$ alkyl, tri-$C_{1-3}$-alkylsilyl, $C_{1-3}$ alkoxy, chloro, and carboxyl, and more preferably with one or more of $C_{1-3}$ alkyl, tri-$C_{1-3}$-alkylsilyl, $C_{1-3}$ alkoxy, and carboxyl. It is preferred that the aryl group is unsubstituted or substituted with carboxyl. It is preferred that n=1 or 2, and more preferably n=1. It is preferred that m=1-4, more preferably m=2-4, and yet more preferably m=2. Preferably, each $R^{10}$ is independently chosen from H, $C_{1-6}$ alkyl, $C_{1-6}$ alkenyl, $C_{1-6}$ alkoxy, carboxy, $C_{2-6}$ carboxy-containing moiety, $C_{2-6}$ keto-containing moiety, $C_{1-6}$ amido-containing moiety, $C_{2-6}$ alkoxyalkanol, and $C_{2-6}$ alkoxyester, and more preferably from H, $C_{1-3}$ alkyl, and $C_{1-3}$ alkoxy. Preferably, $B^1$ comprises one or more carbon-carbon double bonds (ethylenic unsaturation). Suitable single valent $B^1$ groups preferably have the formula—$[C(R^{11})=CR^{12}]_xZ^1$, wherein $R^{11}$ $R^{12}$ are independently chosen from hydrogen, $C_{1-6}$ alkyl, and aryl; Z is chosen from hydrogen, $C_{1-6}$ alkyl, $C_{6-10}$ aryl, siloxaryl, -$CO_2R^{13}$; each $R^{13}$ is independently chosen from H, $C_{1-6}$ alkyl, $C_{1-6}$ hydroxyalkyl, $C_{6-10}$ aryl, $C_{6-10}$ hydroxyaryl, $C_{7-20}$ aralkyl, $C_{7-20}$ hydroxyaralkyl, and $C_{7-20}$ alkaryl; and x=1 or 2. Preferably, $R^{11}$ and $R^{12}$ are independently chosen from H, $C_{1-3}$ alkyl, and aryl, and more preferably H and $C_{1-3}$ alkyl. It is preferred that $R^{13}$ is H, $C_{1-3}$ alkyl, $C_{1-6}$ hydroxyalkyl, $C_{6-10}$ aryl, $C_{6-10}$ hydroxyaryl, and $C_{7-20}$ hydroxyaralkyl. $Z^1$ is preferably siloxyl or —$CO_2R^{13}$. Preferred siloxyl groups have the formula —$[Si(R^{14})_2$—O]p-$Si(R^{14})_2$—, wherein each $R^{14}$ is independently chosen from H, $C_{1-6}$ alkyl, aryl, aralkyl, and alkaryl; and p is an integer from 1 or more. It is preferred that $R^{14}$ is chosen from $C_{1-3}$ alkyl, $C_{6-10}$ aryl, and $C_{7-20}$ aralkyl. Suitable aralkyl groups include benzyl, phenethyl and phenylpropyl.

Preferably, the arylcyclobutene oligomers in the crosslinkable compositions comprise as polymerized units one or more bis-benzocyclobutene monomers of formula (21):

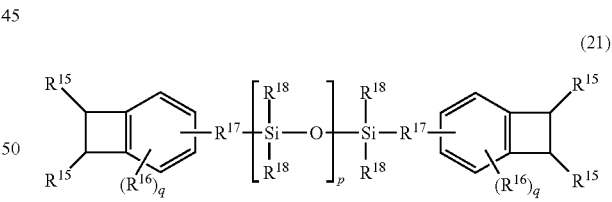

(21)

wherein each $R^{15}$ is independently chosen from H, $C_{1-6}$ alkyl, $C_{1-6}$ alkenyl, $C_{1-6}$ alkoxy, carboxy, $C_{2-6}$ carboxy-containing moiety, $C_{2-6}$ keto-containing moiety, $C_{1-6}$ amido-containing moiety, $C_{2-6}$ alkoxyalkanol, $C_{2-6}$ alkoxyester, and —O—$C_{6-20}$ aryl, —(C=O)—$C_{6-20}$ aryl, —O—(C=O)—$C_{6-20}$ aryl, and —(C=O)—O—$C_{6-20}$ aryl, and preferably from H, $C_{1-3}$ alkyl, and $C_{1-3}$ alkoxy; each $R^{16}$ is independently chosen from $C_{1-6}$ alkyl, tri-$C_{1-6}$-alkylsilyl, $C_{1-6}$ alkoxy, and halo; each $R^{17}$ is independently a divalent, ethylenically unsaturated organic group; each $R^{18}$ is independently chosen from H, $C_{1-6}$ alkyl, $C_{7-20}$ aralkyl and phenyl; p is an integer from 1 or more; and q is an integer from 0 to 3. Each $R^{15}$ is preferably independently chosen from H, $C_{1-3}$ alkyl, and $C_{1-3}$ alkoxy, and more preferably each $R^{15}$ is H. It is preferred that each $R^{16}$ is independently chosen from $C_{1-6}$ alkyl, tri-$C_{1-3}$-alkylsilyl, $C_{1-3}$ alkoxy, and chloro, and more preferably from $C_{1-3}$ alkyl, tri-$C_{1-3}$-alkylsilyl, and $C_{1-3}$ alkoxy. Preferably, each $R^{17}$ is independently chosen from a $C_{2-6}$ alkenyl, and more preferably each $R^{17}$ is —CH=CH—. Each $R^{18}$ is preferably chosen from $C_{1-3}$ alkyl, and more preferably each $R^{18}$ is methyl. Preferably, p=1-5, more preferably p=1-3, and yet more preferably p=1. It is preferred that q=0. A particularly preferred arylcyclobutene monomer, 1,3-bis(2-bicyclo[4.2.0]octa-1,3,5-trien-3-yl ethenyl)—1,1,3,3-tetramethyldisiloxane (DVS-bisBCB), has the formula (22).

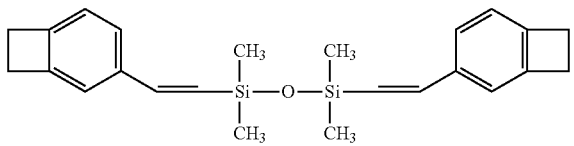

(22)

Also preferred in the crosslinkable compositions are arylcyclobutene oligomers comprising as polymerized units one or more benzocyclobutene monomers of formula (23):

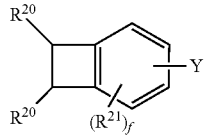

(23)

wherein each $R^{20}$ is independently chosen from H, $C_{1-6}$ alkyl, $C_{1-6}$ alkenyl, $C_{1-6}$ alkoxy, carboxy, $C_{2-6}$ carboxy-containing moiety, $C_{2-6}$ keto-containing moiety, $C_{1-6}$ amido-containing moiety, $C_{2-6}$ alkoxyalkanol, $C_{2-6}$ alkoxyester, —O—$C_{6-20}$ aryl, —(C=O)—$C_{6-20}$ aryl, —O—(C=O)—$C_{6-20}$ aryl, and —(C=O)—O—$C_{6-20}$ aryl, and preferably from H, $C_{1-3}$ alkyl, and $C_{1-3}$ alkoxy; each $R^{21}$ is independently chosen from $C_{1-6}$ alkyl, tri-$C_{1-6}$-alkylsilyl, $C_{1-6}$ alkoxy, and halo; Y is a monovalent radical having from 3 to 15 carbon atoms and having at least one —OH moiety; and f is an integer of from 0 to 2. Each $R^{20}$ is preferably independently chosen from H, $C_{1-3}$ alkyl, and $C_{1-3}$ alkoxy, and more preferably each $R^{20}$ is H. Preferably, each $R^{21}$ is independently chosen from $C_{1-6}$ alkyl, tri-$C_{1-3}$-alkylsilyl, $C_{1-3}$ alkoxy, and chloro, and more preferably from $C_{1-3}$ alkyl, tri-$C_{1-3}$-alkylsilyl, and $C_{1-3}$ alkoxy. The monovalent radical of Y may be aliphatic and/or aromatic. Typically, Y has from 1 to 5 —OH moieties, preferably from 1 to 3, more preferably 1 or 2, and yet more preferably 1 —OH moiety. Y preferably is an ethylenically unsaturated monovalent radical having from 3 to 15 carbon atoms and having at least one —OH moiety. More preferably, the at least one —OH moiety of Y is —$CO_2H$. Preferred compounds of formula (23) are those wherein Y is chosen from —CH=CHC(=O)OR$^{22}$; —CH=CH—$CH_2OH$; —$CH_2$—CH=CHC$_6H_4OH$; and —CH=CHCH$_2$C$_6H_4OH$; wherein $R^{22}$ is chosen from H, $C_{2-8}$ hydroxyalkyl, and $C_{4-8}$ alkyl having one or more quaternary carbons directly bonded to the oxygen of the carboxyl moiety. More preferred are compounds of formula (23) are those wherein Y is —CH=CHC(=O)OR$^{22}$, and yet more preferably —CH=CHC(=O)OH. It is preferred that f=0. It is further preferred that the arylcyclobutene oligomers of formula (20) comprise as polymerized units one or more bis-benzocyclobutene monomers of formula (21) and one or more monomers of formula (23).

Arylcyclobutene oligomers may be prepared by any suitable means, such as those described in U.S. Pat. Nos. 4,812,588; 5,136,069; 5,138,081; and Int. Pat. App. No. WO 94/25903. Suitable arylcyclobutene oligomers are also commercially available under the CYCLOTENE™ brand, available from Dow Electronic Materials.

The oligomer material may be used in the present crosslinkable compositions in an amount from 1 to 99 wt % by solids, preferably from 15 to 75 wt %, and more preferably from 25 to 75 wt %. When a mixture of different arylcyclobutene materials, such as at least two arylcyclobutene crosslinkers or at least two arylcyclobutene oligomers or a mixture of arylcyclobutene crosslinkers and arylcyclobutene oligomers, is used, any suitable ratio of one arylcyclobutene material to another arylcyclobutene material may be used, such as 1:99 to 99:1.

Suitable optional additives useful in the present crosslinkable compositions include, without limitation, one or more of each of curing agents, surfactants, secondary crosslinkers different from the present monomers, non-crosslinking monomers, inorganic fillers, organic fillers, plasticizers, adhesion promoters, metal passivating materials, and the like, and combinations of the foregoing. Suitable surfactants are well-known to those skilled in the art, and nonionic surfactants are preferred. Such surfactants may be present in an amount of from 0 to 10 g/L, and preferably from 0 to 5 g/L. Any suitable inorganic fillers may optionally be used in the present compositions, and are well-known to those skilled in the art. Exemplary inorganic fillers include, but are not limited to, silica, silicon carbide, silicon nitride, alumina, aluminum carbide, aluminum nitride, zirconia, and the like, and mixtures thereof. The inorganic filler may be in the form of a powder, rods, spheres, or any other suitable shape. Such inorganic filler may have any suitable dimensions. Inorganic filler may be used in an amount of from 0 to 80 wt %, based on the total weight of the composition. Any crosslinking monomer that is different from the monomers of the invention may be used as secondary crosslinkers, provided that they crosslink with the benzocyclobutene-based components in the composition under the conditions used to cure the composition. Suitable secondary crosslinkers include, but are not limited to, polyamines, polythiols, and (meth)acrylate-containing crosslinkers. The selection of such secondary crosslinkers is within the ability of those skilled in the art. Such secondary crosslinkers are typically used in an amount of from 0 to 20 wt %, and preferably 0 to 10 wt %, based on the total weight of the polymerizable components in the composition. One or more non-crosslinking monomers may also be added to the present compositions, and are typically present in an amount of from 0 to 20 wt %, based on the total weight of the polymerizable components in the composition. Such non-crosslinking monomers contain 1 or 2 polymerizable moieties capable of polymerizing with the benzocyclobutene-based components in the present compositions. Preferably, the metal passivating material is a copper passivating agent. Suitable copper passivating agents are well known in the art and include imidazoles and benzotriaoles.

A variety of curing agents may be used in the present crosslinkable compositions. Suitable curing agents may aid in the curing of the benzocyclobutene-based materials, and may be activated by heat or light. Exemplary curing agents include, but are not limited to, thermally generated initiators and photoactive compounds (photogenerated initiators). The selection of such curing agents is within the ability of those skilled in the art. Preferred curing agents are photoactive compounds, and more preferably diazonaphthoquinone (DNQ) compounds including sulfonate esters of a DNQ compound. Suitable DNQ compounds are any compounds having a DNQ moiety, such as a DNQ sulfonate ester moiety, and that function as photoactive compounds in the present compositions, that is, they function as dissolution inhibitors upon exposure to appropriate radiation. Suitable DNQ compounds are disclosed in U.S. Pat. Nos. 7,198,878 and 8,143,360. The amount of photoactive compound varies from 0 to 30 wt %, based on the total weight of the benzocyclobutene-based components. When present, the photoactive component is typically used in an amount of 5 to 30 wt %, preferably from 5 to 25 wt %, and more preferably from 10 to 25 wt %, based on the total weight of the benzocyclobutene-based components.

Any suitable adhesion promoter may be used in the present compositions and the selection of such adhesion promoter is well within the ability of those skilled in the art. Preferred adhesion promoters are silane-containing materials, and more preferably trialkoxysilane-containing materials. Exemplary adhesion promoters include, but are not limited to: bis(trialkoxysilylalkyl)benzenes such as bis(trimethoxysilylethyl)benzene; aminoalkyl trialkoxy silanes such as aminopropyl trimethoxy silane, aminopropyl triethoxy silane, and phenyl aminopropyl triethoxy silane; and other silane coupling agents, as well as mixtures of the foregoing. Particularly suitable adhesion promoters include AP 3000, AP 8000, and AP 9000S, available from Dow Electronic Materials (Marlborough, Mass.). The present crosslinkable compositions typically contain from 0 to 15 wt % of an adhesion promoter based on the total weight of the composition, preferably from 0.5 to 10 wt %, more preferably from 1 to 10 wt %, yet more preferably from 5 to 10 wt %.

The present crosslinkable compositions are prepared by combining the one or more present monomers, the one or more oligomers, and any optional organic solvents or additional components in any order. When the present crosslinkable compositions contain a curing agent such as a photoactive compound, it is preferred that the curing agent is first dissolved in a suitable organic solvent, then combined with one or more present monomers and any optional surfactant, and then combined with one or more oligomers and any optional adhesion promoter.

Any of the present compositions comprising one or more of the present monomers and one or more organic solvents, and optionally containing one or more oligomers, are useful in forming a layer of a benzocyclobutene polymer having improved flexibility on a substrate. Such benzocyclobutene polymer layers are suitable as dielectric layers, permanent bonding adhesives, as stress buffer layers, and the like. The present compositions may be coated on a substrate by any suitable method. Suitable methods for disposing the present compositions include, but are not limited to, spin-coating, curtain coating, spray coating, roller coating, dip coating, vapor deposition, and lamination such as vacuum lamination, among other methods. In the semiconductor manufacturing industry, spin-coating is a preferred method to take advantage of existing equipment and processes. In spin-coating, the solids content of the composition may be adjusted, along with the spin speed, to achieve a desired thickness of the composition on the surface it is applied to. Typically, the present compositions are spin-coated at a spin speed of 400 to 4000 rpm. The amount of the present compositions dispensed on the wafer or substrate depends on the total solids content in the composition, the desired thickness of the resulting layer, and other factors well-known to those skilled in the art. When a film or layer of the present compositions is cast, such as by spin-coating, much (or all) of the solvent evaporates during deposition of the film. Preferably, after being disposed on a surface, the composition is heated (baked) to remove any remaining solvent. Typical baking temperatures are from 90 to 160° C., although other temperatures may be suitably used. Such baking to remove residual solvent is typically done for approximately 2 minutes, although longer or shorter times may suitably be used. The arylcyclobutene oligomers are typically cured by heating for a period of time. Suitable curing temperatures range from 180 to 250° C. or higher. Typically curing times range from 1 to 600 minutes.

In an alternate preferred method, the present crosslinkable compositions may be formed as a dry film and is disposed on the surface of a substrate by lamination. A variety of suitable lamination techniques, including vacuum lamination techniques, may be used and are well known to those skilled in the art. In forming a dry film, the present compositions are first disposed onto a front surface of a suitable film support sheet such as a polyester sheet, preferably polyethyleneterephthalate (PET) sheet, or a polyimide sheet such as KAPTON™ polyimide, using slot-die coating, gravure printing, or another appropriate method. The composition is then soft baked at a suitable temperature, such as from 90 to 140° C., for an appropriate time, such as from 1 to 30 minutes, to remove any solvent. A polymer film cover sheet such as polyethylene is then roll-laminated at room temperature onto the dried composition to protect the composition during storage and handling. To dispose the dried composition onto the substrate, the cover sheet is first removed. Then, the dried composition on the support sheet is laminated onto the substrate surface using roll-lamination or vacuum lamination. The lamination temperature can range from 20 to 120° C. The support sheet is then removed (peeled), leaving the dried composition on that surface.

A wide variety of electronic device substrates may be employed in the present invention. An electronic device substrate is any substrate for use in the manufacture of any electronic device. Exemplary electronic device substrates include, without limitation, semiconductor wafers, glass, sapphire, silicate materials, silicon nitride materials, silicon carbide materials, display device substrates, epoxy mold compound wafers, circuit board substrates, and thermally stable polymers. As used herein, the term "semiconductor wafer" is intended to encompass a semiconductor substrate, a semiconductor device, and various packages for various levels of interconnection, including a single-chip wafer, multiple-chip wafer, packages for various levels, substrates for light emitting diodes (LEDs), or other assemblies requiring solder connections. Semiconductor wafers, such as silicon wafers, gallium-arsenide wafers, and silicon-germanium wafers, may be patterned or unpatterned. As used herein, the term "semiconductor substrate" includes any substrate having one or more semiconductor layers or structures which include active or operable portions of semiconductor devices. The term "semiconductor substrate" is defined to mean any construction comprising semiconductive material, such as a semiconductor device. A semiconductor device refers to a semiconductor substrate upon which at least one microelectronic device has been or is being fabricated. Thermally stable polymers include, without limitation, any polymer stable to the temperatures used to cure the arylcyclobutene material, such as polyimide (for example, KAPTON™ polyimide, available from DuPont, Wilmington, Del.).

When compositions of the invention which do not contain an adhesion promoter are used, the surface of the substrate to be coated with the present compositions may optionally first be contacted with a suitable adhesion promoter or vapor treated. Such treatments improve the adhesion of the present arylcyclobutene polymers to the substrate surface. Any suitable method, such as spin-coating, dip coating, spray coating, curtain coating, roll coating, vapor deposition, and the like, may be used to contact the substrate surface with the adhesion promoter. Spin-coating is a preferred method for contacting the substrate surface with an adhesion promoter. Any suitable adhesion promoter may be used and the selection of such adhesion promoter is well within the ability of those skilled in the art. Preferred adhesion promoters are silane-containing materials, and more preferably trialkoxysilane-containing materials. Exemplary adhesion promoters useful to pre-treat the substrate surface are those described above. Various vapor treatments known in the art may be used to increase the adhesion of the arylcyclobutene polymers of the present invention to the substrate surface, such as plasma treatments. In certain applications, it may be preferred to use an adhesion promoter to treat the substrate surface prior to coating the surface with the present compositions.

The present monomers are useful in forming benzocyclobutene-based polymers that have improved flexibility as compared to conventional benzocyclobutene-based polymers. Accordingly, wafers coated with benzocyclobutene-based polymers comprising as polymerized units one or more monomers of the invention show reduced wafer bow as compared to the same wafers coated with conventional benzocyclobutene-based polymers.

EXAMPLE 1

Synthesis of Trimethylolpropane Propoxylate Tri(Acrylatebenzocyclobutene)—Compound (9)

A 2000 mL three-necked, round bottomed flask with bottom drain port, outfitted with a mechanical stirrer, pressure equalizing addition funnel and condenser with attached nitrogen inlet was charged with potassium acetate (125.6 g, 1.28 mol) and deionized (DI) water (60 mL). The solution was stirred for 10 min. and then trimethylolpropane propoxylate triacrylate having an average of 2 propoxylate groups (107.1 g, 165.9 mmol), 100 mL dimethylformamide (DMF), palladium acetate (0.27 g, 1.18 mmol) and tri(o-tolyl)phosphine (1.14 g, 3.75 mmol) were added to the vessel and the mixture was sparged with nitrogen with stirring for 30 min. The pressure equalizing addition funnel was charged with a solution of 3-bromobenzocyclobutane (91.46 g, 499.6 mmol) in DMF (50 mL). This solution was then de-gassed via nitrogen sparge for 20 min. The reaction solution was slowly heated to 80° C. followed by slow addition of the 3-bromobenzocyclobutane. Reaction completeness was monitored by the disappearance of 3-bromobenzocyclobutane via gas chromatography, which took 27 hr. Toluene (200 mL) was added to the solution which was then cooled to room temperature. The aqueous layer, which was laden with suspended solids, was removed via the reactor bottom drain. The organic layer was filtered over a pad of celite via vacuum filtration. The filtrate was washed with deionized water, resulting in an emulsion which would not separate. The emulsion was filtered again through celite to separate the organic and aqueous layers. The organic layer was isolated, dried over anhydrous magnesium sulfate, filtered and condensed to afford the product as a clear yellow colored viscous oil. Yield: 140.4 g (88.9%).

EXAMPLES 2-5

The procedure of Example 1 was repeated except that the trimethylolpropane propoxylate triacrylate having an average of 2 propoxylate groups was replaced with trimethylolpropane triacrylate (no ethoxylate groups, Compound 10) or with trimethylolpropane ethoxylate triacrylate having the average number of ethoxylated groups indicated in Table 1.

TABLE 1

| Example | Compound No. | Average Ethoxylate Chain Length |
| --- | --- | --- |
| 2 | 6 | 1 |
| 3 | 7 | 2 |
| 4 | 8 | 5 |
| 5 | 10 | 0 |

EXAMPLE 6

A 500 mL two-necked, round bottomed flask with rubber septum and condenser with attached nitrogen inlet was charged with 3-acrylic acid benzocyclobutene (30.17 g, 173.2 mmol), chloroform (100 mL) and DMF (0.10 mL). A solution of thionyl chloride (23.60 g, 198.4 mmol) in chloroform (20 mL) was added via syringe over 15 min. The solution was stirred for 60 min. at room temperature followed by heating to 45° C. for 1 hr. Toluene (75 mL) was added to the vessel and the solution condensed on a rotary evaporator to afford benzocyclobutene acryloyl chloride (BCB-AA acid chloride) as a light tan colored solid in quantitative yield. $^1$H NMR (500 MHz, Chloroform-d) δ 7.83 (d, J=15.5 Hz, 1H), 7.41 (dd, J=7.6, 1.4 Hz, 1H), 7.29 (dd, J=1.3, 0.7 Hz, 1H), 7.13 (dd, J=7.6, 0.9 Hz, 1H), 6.59 (d, J=15.4 Hz, 1H), 3.24 (s, 4H).

EXAMPLE 7

Synthesis of Pentaerythritol Triallyl Ether—Benzocyclobutene Acrylic Acid—Compound (3)

A 1000 mL three necked round bottomed flask outfitted with a mechanical stirrer (Teflon paddle), a pressure equalizing addition funnel was charged with pentaerythritol triallyl ether (NEOALLYL P-30) (111.9 g, 436.5 mmol), toluene (300 mL) and triethylamine (56.61 g, 559.4 mmol). The addition funnel was charged with a solution of BCB-AA acid chloride (88.96 g, 461.8 mmol) from Example 6 in toluene (100 mL), which was then added dropwise to the reaction mixture over 45 min. The solution was then heated to 90° C. for 9.5 hr. The solution was then filtered through a 38 mm (1.5 inch) thick silica gel plug on a 350 mL fritted glass funnel. Hexane:ethyl acetate (80:20, 200 mL) was used as the washing solvent. The filtrate was condensed to afford an orange colored viscous oil, which was taken up in hexanes (300 mL) and placed into a freezer for 3 days. The solution was filtered and condensed to afford the product as a viscous dark yellow colored oil. Yield: 178.0 g (93.97%). $^1$H NMR (500 MHz, Chloroform-d) δ 7.67 (dd, J=15.9, 3.1 Hz, 1H), 7.36 (dd, J=7.6, 1.5 Hz, 1H), 7.31-7.18 (m, 1H), 7.13-6.94 (m, 1H), 6.39 (d, J=16.0 Hz, 1H), 5.97-5.78 (m, 2H), 5.27 (dd, J=17.3, 1.7 Hz, 2H), 5.15 (dd, J=10.5, 1.6 Hz, 2H), 4.30 (s, 2H), 3.97 (d, J=5.4 Hz, 4H), 3.52 (s, 4H), 3.20 (s, 3H).

EXAMPLE 8

Synthesis of Trimethyolpropane Allyl Ether—Bis(Benzocyclobutene Acrylic Acid)—Compound (5)

A 500 mL two-necked, round bottomed flask with magnetic stir bar, rubber septum and condenser with attached nitrogen inlet served as the vessel for this reaction. The vessel was charged with BCB-AA acid chloride (28.59 g, 148.4 mmol) from Example 6, toluene (150 mL), triethylamine (19.35 g, 191.2 mmol) and trimethyolpropane allyl ether (27.62 g, 128.9 mmol). The solution was heated to 50° C. for 3 hr. after which time a catalytic amount of DMAP was added. The solution was heated for an additional 5 hr. at 50° C. and then filtered while hot. The filtrate was washed with deionized water and a saturated ammonium chloride solution. The organic layer was isolated, dried over anhydrous magnesium sulfate, filtered and condensed to afford the crude material which was purified by automated flash chromatography on silica gel. The resulting product was then taken up into ethyl acetate:hexanes (20:80, 200 mL) and placed in a freezer for 48 hr. The solution was then filtered and condensed in-vacuo. The resulting oil was taken up into dichloromethane (200 mL) and washed with a saturated sodium bicarbonate solution doped with 1% NaOH. The organic layer isolated, dried over anhydrous magnesium sulfate, filtered and condensed to afford the product Compound (5) as a clear yellow colored oil. Yield: 34.65 g (72.4%). $^1$H NMR (500 MHz, Chloroform-d) δ 7.67 (d, J=15.9 Hz, 1H), 7.36 (d, J=7.4 Hz, 1H), 7.26 (s, 1H), 7.07 (d, J=7.5 Hz, 1H), 6.39 (d, J=16.0 Hz, 1H), 5.89 (ddt, J=17.3, 10.6, 5.4 Hz, 2H), 5.27 (dd, J=17.3, 1.7 Hz, 2H), 5.16 (dd, J=10.4, 1.7 Hz, 2H), 4.19 (d, J=1.0 Hz, 2H), 3.97 (d, J=5.4 Hz, 4H), 3.40 (s, 4H), 3.20 (s, 4H), 1.52 (q, J=7.5 Hz, 2H), 0.91 (t, J=7.5 Hz, 3H).

EXAMPLE 9

Synthesis of Trimethylolpropane Diallyl Ether—Benzocyclobutene Acrylic Acid—Compound (4)

The procedure of Example 8 was repeated except that the following amounts of materials were used: BCB-AA acid chloride from Example 6 (40.98 g, 212.7 mmol), toluene (200 mL), triethylamine (29.11 g, 287.7 mmol) and trimethylolpropane allyl ether (18.18 g, 104.3 mmol). The product was isolated as a clear orange colored viscous oil. Yield: 36.02 g (71.6%). $^1$H NMR (500 MHz, Chloroform-d) δ 7.68 (d, J=15.9 Hz, 2H), 7.35 (dd, J=7.6, 1.4 Hz, 2H), 7.24 (s, 2H), 7.06 (d, J=7.6 Hz, 2H), 6.39 (d, J=16.0 Hz, 2H), 5.89 (ddt, J=17.2, 10.7, 5.5 Hz, 1H), 5.37-5.23 (m, 1H), 5.17 (dd, J=10.4, 1.6 Hz, 1H), 4.25 (d, J=2.1 Hz, 4H), 3.98 (d, J=5.5 Hz, 2H), 3.44 (s, 2H), 3.19 (s, 8H), 1.59 (q, J=7.6 Hz, 2H), 0.96 (t, J=7.6 Hz, 3H).

EXAMPLE 10

Synthesis of Compound (24)

A 500 mL two-necked, round bottomed flask with a magnetic stir bar, rubber septum and condenser with attached nitrogen inlet was charged with BCB-AA acid chloride from Example 6 (13.91 g, 72.2 mmol), toluene (150 mL) and triethylamine (8.86 g. 87.6 mmol). Amine terminated propoxylated trimethylolpropane having a total of 5-6 propoxylate groups (JEFFAMINE™ T-403, Huntsman Corporation) (10.33 g, 21.5 mmol) was then added to the solution via syringe through the rubber septum. The solution was then heated to 90° C. for 8 hr. The solution was filtered while hot, washed with dilute (1 wt %) NaOH , dried over anhydrous magnesium sulfate, filtered and condensed. The isolated material was then purified via automated flash chromatography over silica gel. The resulting product (Compound 24) was a yellow colored solid. Yield: 13.89 g (68.0%). $^1$H NMR (400 MHz, Chloroform-d) δ 7.56 (d, J=15.7 Hz, 3H), 7.27 (s, 3H), 7.15 (d, J=7.3 Hz, 3H), 6.98 (d, J=7.7 Hz,3), 6.53-6.08 (m, 3H), 4.33-4.06 (m, 3H), 3.68-3.21 (m, 18H), 3.19-2.99 (m, 12H), 1.49-1.33 (m, 2H), 1.30-0.99 (m, 9H), 0.93-0.67 (m, 3H).

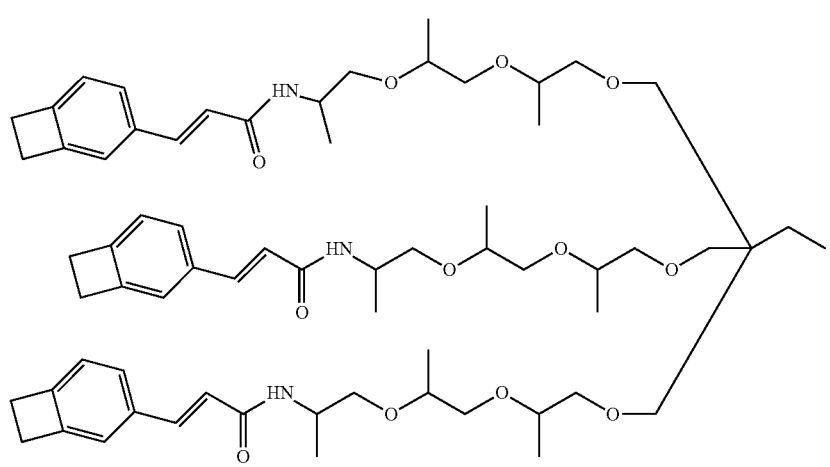

(24)

EXAMPLES 11-14

Synthesis of Compounds (25-28)

The general procedure of Example 9 was repeated except that BCB-AA acid chloride from Example 6 was reacted with each of the following polyol compounds to provide Compounds (25-28). For each of Compounds (25-27), 3 equivalents of BCB-AA acid chloride were used for each equivalent of polyol compound, and 4 equivalents of BCB-AA acid chloride were used to prepare Compound (28).

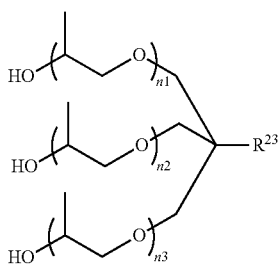

TABLE 2

| Example No. | Compound No. | $R^{23}$ | Σ n1 + n2 + n3 + n4 |
|---|---|---|---|
| 11 | 25 | $C_2H_5$ | 4-5 |
| 12 | 26 | H | 10-11 |
| 13 | 27 | H | 16-18 |
| 14 | 28 | $-CH_2O(CH_2CH(CH_3))_{n4}OH$ | 6-7 |

EXAMPLE 15

Synthesis of Compound (29)

The general procedure of Example 9 was repeated except that 4 equivalents of BCB-AA acid chloride from Example 6 were reacted with pentaerythritol to provide Compound (29).

EXAMPLE 16

Synthesis of 1-MeO-Tris-Benzocyclobutene-Acrylate—Compound (11)

Bromobenzocyclobutene (91.5 g, 0.5 mol) and chlorobenzene(anhydrous, 2500 mL) were charged into a four-neck 5 L flask equipped with mechanical stir, condenser, $N_2$ (in and outlet) and thermometer. The reaction mixture was heated to 120° C., and N-bromosuccinimide (111.3 g, 0.625 mol) was gradually charged over 30 min., followed by slowly feeding a mixture of a free radical azo compound source (V$_{AZO}$™ 68) (14.0 g, 0.05 mol) and chlorobenzene (500 mL) over 30 min. Then the reaction mixture was heated to 133° C. (mild reflux) and kept at that temperature for 6 hr. The mixture was then cooled to room temperature overnight, and chlorobenzene was removed by vacuum evaporation. The crude product was extracted with hexane. After removal of hexane, 1-bromo-bromobenzocyclobutene (1-Br-BrBCB) (80-85° C./0.35 torr, 90 g, ca. 93% purity) was obtained by vacuum distillation.

The 1-Br-BrBCB (90.0 g, 0.49 mol), anhydrous THF (100 mL), and sodium methoxide (200 g, 0.93 mol, 2-5 wt % in methanol) were charged into a 1000 mL four-neck flask equipped with a condenser, $N_2$ (in and outlet), and mechanical stirrer. The reaction mixture was heated to 75° C. and held at this temperature for 6 hr. After reaction, the reaction mixture was poured into 400 mL of hexane, and washed with DI water six times (6×100 mL). The solvent in the separated organic layer was removed by evaporator, and the colorless product 1-methoxy-bromobenzocyclobutene (1-MeO-BrBCB) was obtained by vacuum distillation (80 g, 62-65° C./0.39 torr, yield, 76%).

Trimethylolpropane propoxylate triacrylate (TMPPTA, 32.24 g, 0.05 mol), toluene (anhydrous, 30 g), N-methyldicyclohexylamine (39.07 g, 0.20 mol) were charged into a 500 mL four-neck flask equipped with additional funnel, $N_2$ (in and outlet), and magnetic stirrer, and thermometer. 1-MeO-BrBCB (32.0 g, 0.15 mol) and toluene (anhydrous, 30 g) were charged into an addition funnel, followed by $N_2$ bubbling for 20 min. In a dry glove box, a catalyst solution of tris(dibenzylideneacetone)dipalladium (0.916 g, 1.0 mmol), tri-tert-butylphosphine (0.425 g, 2.1 mmol) and toluene (anhydrous, 20 g) was prepared. This catalyst solution was stirred for 20 min. under $N_2$, and then transferred into the reaction flask via a syringe. Next, the MeO-BrBCB/toluene solution was added dropwise from the additional funnel over 60 min. After addition was complete, the reaction mixture was stirred at room temperature for 48 hr. After reaction, the reaction mixture was poured into 500 mL of hexane, and washed with DI water (100 mL water with 5 mL acetic acid) six times (6×100 mL). The resulted product (Compound 11) (43 g, yield, 82%) was obtained by removing solvent (toluene, hexane) under vacuum.

EXAMPLE 17

Synthesis of Pentaerythritol Tris(1-MeO-BCB) Allyl Ether—Compound (16)

Pentaerythritol triallylether (N$_{EOALLYL}$ P-30, 12.72 g, 0.05 mol), toluene (anhydrous, 30 g), and N-methyldicyclohexylamine (39.07 g, 0.20 mol) were charged into a 500 mL four-neck reaction flask equipped with an addition funnel, $N_2$ (in and outlet), magnetic stirrer, and thermometer. 1-MeO-BrBCB (32.0 g, 0.15 mol) and toluene (anhydrous, 30 g) were charged into an addition funnel, followed by $N_2$ bubbling for 20 min. In a dry glove box, a catalyst solution of tris(dibenzylideneacetone)dipalladium (0.916 g, 1.0 mmol), tri-tert-butylphosphine (0.425 g, 2.1 mmol) and toluene (anhydrous, 20 g) was prepared. This catalyst solution was stirred for 20 min. under $N_2$, and then transferred into the reaction flask via a syringe. 1-MeO-BrBCB/toluene solution was dropwise added to the flask over 60 min. After addition was complete, the reaction mixture was kept stirring at room temperature for 48 hr. After reaction, the reaction mixture was poured into 500 mL of hexane, and washed with DI water (100 mL water with 5 mL acetic acid) 6 times (6×100 mL). The resulting product (Compound 16) (37 g, yield, 82%) was obtained by removing solvent (toluene, hexane) under vacuum.

EXAMPLE 18

Preparation of Formulation 1

In a 250 mL brown bottle, 6.16 g of 2,1,5-diazonaphthoquinone (DNQ) sulfonic ester of 4,4'—((2-hydroxyphenyl)

methylene)bis(2,3,6-trimethylphenol) with an average 65 mole % of esterified phenols as photoactive compound (PAC) was dissolved in 1.39 g dipropylene glycol dimethyl ether (PROGLYDE™ DMM, The Dow Chemical Company), 3.75 g methyl 3-methoxypropionate (MMP) and 0.16 g propylene glycol methyl ether acetate (PGMEA) and 2.64 g of a 5 wt % solution of a silicon-containing surfactant (DCT L-7604) in MMP solvent. Next, 23.32 g of a 50 wt % solution of Compound (25) from Example 11 in MMP as crosslinker was added along with 57.30 g of a 40.85 wt % arylcyclobutene oligomer solution in PROGLYDE DMM solvent and 5.28 g of a 50 wt % triethoxysilylpropylmaleamic acid in PGMEA as adhesion promoter. The arylcyclobutene oligomer solution was a B-staged reaction mixture with on average 69 mole % benzocyclobutene acrylic acid (BCB-AA) and 31 mole % bis(benzocyclobutene vinyl) dimethylsiloxane (DVS-BCB). The bottle was rolled for 12 hours to form a homogeneous solution. After de-foaming, the solution was filtered through a 0.45 µm nylon filter before use.

EXAMPLES 19-22

Formulations 2-5

The procedure of Example 18 was repeated except that the crosslinker solution was a 50 wt % MMP solution the compounds shown in Table 3.

TABLE 3

| Example | Formulation No. | Compound No. |
|---|---|---|
| 19 | 2 | 26 |
| 20 | 3 | 27 |
| 21 | 4 | 28 |
| 22 | 5 | 29 |

EXAMPLE 23

Formulation 6

The procedure of Example 18 was repeated except that the crosslinker solution used was replaced with 23.51 g of a 39.68 wt % solution of an oligomer comprising only as polymerized units a monomer of Compound 25 in PROGLYDE DMM solvent.

EXAMPLE 24

Formulation 7

The procedure of Example 18 was repeated except that the crosslinker solution used was replaced with 23.54 g of a 39.62 wt % solution of an oligomer comprising only as polymerized units a monomer of Compound 25 in 3-methoxy-1-butyl acetate.

EXAMPLE 25

Solutions of each of Formulations 1-7 and a Control sample were spin coated on 200 mm prime grade silicon wafers using a Site Trac TT5-XP coater at 1450 rpm for 30 seconds followed by a hotplate bake of 120° C. for 90 seconds to further remove solvent. The film thickness was approximately 6.5 µm. The coated wafers were then thermally cured in a Blue M Ultra-Temp oven (Model IGF-6680F-4) under nitrogen at 200° C. for 100 min. Oxygen levels were maintained at <100 ppm for the entire process. The final film thickness was approximately 6.1 µm. Film stress was measured within 2 hr. of removal from the furnace. The Control sample was a commercially available benzocyclobutene material, CYCLOTENE™ 6505, available from Dow Electronic Materials. The Control did not contain any monomers of the invention, nor any oligomers comprising any monomers of the invention.

Residual stress of the cured polymeric film was measured on a FLX-3300-T Thin Film Stress Measurement System from TOHO Technology. Duplicate wafers were prepared for each Formulation and the average of two measurements was reported as the residual stress value. The residual stress $\sigma_{film}$ is defined in Equation 1.

$$\sigma_{film} = \left(\frac{E}{1-v}\right)\frac{t_s^2}{6t_f R} \quad \text{Equation 1}$$

where $\sigma_{film}$ is residual stress, $t_s$ is thickness of the silicon substrate, $t_f$ is the coating thickness, and R is the radius as defined in Equation 2. E is the Modulus of Silicon and v is Poisson's ratio. These values are constant and are defined as E=169.0 GPa and v=0.0641 (See Hopcroft, MA, J. Micromechanical Systems, Vol 19, No 2, April 2010. Page 237, Table V.).

$$R = \frac{L^2}{8B} \quad \text{Equation 2}$$

L is the scan length and B is the wafer bow, which is defined as the deviation of the center point of the median surface of a free, un-clamped wafer from the median surface to the reference plane. The residual stress values for the polymer films from each of Formulations 1-7 and the Control are reported in Table 4. As can be seen from these data, the compositions of the present invention provide significant reduction in residual stress as compared to the commercially available Control.

TABLE 4

| Formulation No. | Stress Value (MPa) |
|---|---|
| 1 | 24.08 |
| 2 | 20.51 |
| 3 | 16.18 |
| 4 | 24.95 |
| 5 | 24.14 |
| 6 | 24.77 |
| 7 | 24.46 |
| Control | 29.05 |

EXAMPLE 26

Synthesis of Compounds (30-39)

The general procedure of Example 1 is repeated except that equivalents of 3-bromobenzocyclobutane used is varied and/or the trimethylolpropane propoxylate triacrylate having an average of 2 propoxylate groups is replaced with trimethylolpropane triacrylate, pentrerythritol triacrylate, pentaerythritol tetraacrylate, or propoxylated pentaerythritol tetraacrylate and is expected to prepare Compounds (30-39) having the following general formula as described in Table 5.

ing general formula as described in Table 6 where $\Sigma$ AG is the sum of the terminal acrylate groups, or $[(3-(k+a))+(3-(z+u))]$.

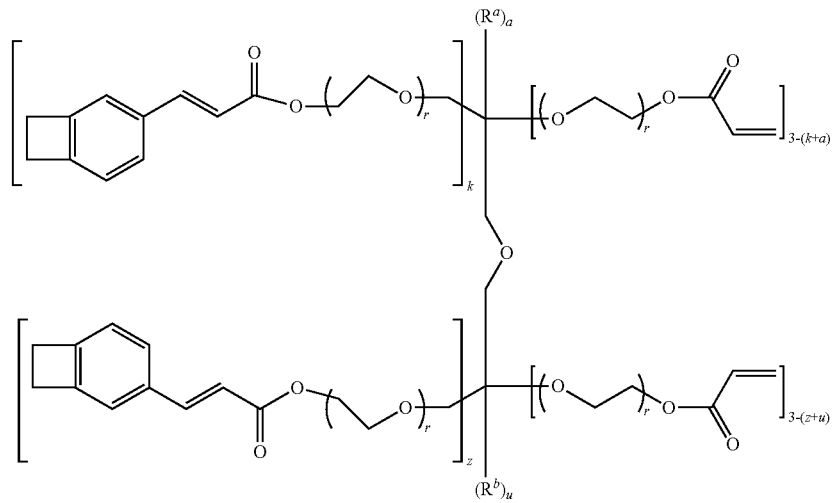

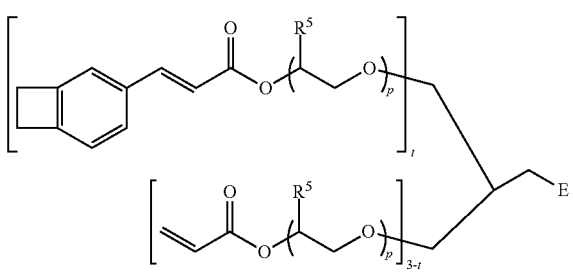

TABLE 5

| Compound | p | t | $R^5$ | E |
|---|---|---|---|---|
| 30 | 2 | 1 | $CH_3$ | $CH_3$ |
| 31 | 2 | 2 | $CH_3$ | $CH_3$ |
| 32 | 0 | 2 | — | $CH_3$ |
| 33 | 1 | 2 | H | $CH_3$ |
| 34 | 0 | 2 | — | OH |
| 35 | 0 | 1 | — | —O—(C=O)—CH=$CH_2$ |
| 36 | 0 | 2 | — | —O—(C=O)—CH=$CH_2$ |
| 37 | 0 | 3 | — | —O—(C=O)—CH=$CH_2$ |
| 38 | 1 | 1 | $CH_3$ | —O—CH($CH_3$)—$CH_2$—O—(C=O)—CH=$CH_2$ |
| 39 | 1 | 2 | $CH_3$ | —O—CH($CH_3$)—$CH_2$—O—(C=O)—CH=$CH_2$ |

TABLE 6

| Compound | r | $\Sigma k + z$ | a | u | $\Sigma$ AG | $R^a$ | $R^b$ |
|---|---|---|---|---|---|---|---|
| 40 | 0 | 1 | 1 | 1 | 3 | —$C_2H_5$ | —$C_2H_5$ |
| 41 | 0 | 2 | 1 | 1 | 2 | —$C_2H_5$ | —$C_2H_5$ |
| 42 | 0 | 3 | 1 | 1 | 1 | —$C_2H_5$ | —$C_2H_5$ |
| 43 | 0 | 1 | 1 | 0 | 4 | —$CH_2OH$ | — |
| 44 | 0 | 2 | 1 | 0 | 3 | —$CH_2OH$ | — |
| 45 | 0 | 3 | 1 | 0 | 2 | —$CH_2OH$ | — |
| 46 | 1 | 1 | 1 | 0 | 4 | —$CH_2OH$ | — |
| 47 | 1 | 2 | 1 | 0 | 3 | —$CH_2OH$ | — |
| 48 | 1 | 4 | 1 | 0 | 1 | —$CH_2OH$ | — |
| 49 | 2 | 1 | 1 | 0 | 4 | —$CH_2OH$ | — |
| 50 | 2 | 2 | 1 | 0 | 3 | —$CH_2OH$ | — |
| 51 | 0 | 1 | 0 | 0 | 5 | — | — |
| 52 | 0 | 2 | 0 | 0 | 4 | — | — |
| 53 | 0 | 3 | 0 | 0 | 3 | — | — |
| 54 | 0 | 5 | 0 | 0 | 1 | — | — |

EXAMPLE 27

Synthesis of Compounds (40-54)

The general procedure of Example 1 is repeated except that equivalents of 3-bromobenzocyclobutane used is varied and the trimethylolpropane propoxylate triacrylate having an average of 2 propoxylate groups is replaced with dipentaerythritol pentaacrylate, ditrimethylolpropane tetraacrylate, or ethoxylated dipentaerythritol pentaacrylate and is expected to prepare Compounds (40-54) having the follow-

EXAMPLES 28

Formulations 8-10

The procedure of Example 18 is repeated with similar results expected except that the crosslinker solution is a 50 wt % MMP solution the compounds shown in Table 7.

TABLE 7

| Example | Formulation No. | Compound No. |
|---|---|---|
| 28 | 8 | 31 |
| 29 | 9 | 35 |
| 30 | 10 | 38 |
| 31 | 11 | 42 |
| 32 | 12 | 47 |

What is claimed is:

1. A compound of the formula (1)

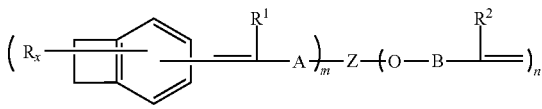

wherein each A is independently chosen from —CR³R⁴—O—, —C(=O)O—, and —C(=O)NH—; each B is independently chosen from —CR³R⁴— and —C(=O)—; each R is independently chosen from halo, cyano, hydroxy, carboxy, $C_{1-6}$ alkoxy, $C_{1-6}$ alkyl, $C_{1-6}$ haloalkyl, $C_{2-6}$ alkenyl, carboxy $C_{1-6}$ alkyl, —(C=O)—$C_{1-6}$ alkyl, —G—(C=O)—$C_{1-6}$ alkyl, —(C=O)—G—$C_{1-6}$ alkyl, —O—$C_{4-20}$ aryl, —(C=O)—$C_{4-20}$ aryl, —G—(C=O)—$C_{4-20}$ aryl, and —(C=O)—G—$C_{4-20}$ aryl; each of R¹, R², R³ and R⁴ is independently chosen from H, $C_{1-10}$ alkyl, $C_{2-10}$ alkenyl, $C_{2-10}$ alkynyl, and $C_{4-15}$ aryl; Z is an organic radical having 2 to 50 carbon atoms; G is O or N(R')₂; each R' is independently chosen from H, $C_{1-6}$ alkyl, $C_{4-10}$ aryl, and $C_{7-15}$ aralkyl; x is the number of R groups and is an integer of from 0 to 2; m is an integer of from 1 to 6; n is an integer of from 0 to 5; and m+n=3 to 6.

2. The compound of claim 1 wherein m=1 to 4.
3. The compound of claim 1 wherein n=0 to 3.
4. The compound of claim 1 wherein A is —CR³R⁴—O— or —C(=O)O—.
5. The compound of claim 1 wherein Z has one or more ether linkages, one or more hydroxyl moieties, or a combination of one or more ether linkages and one or more hydroxyl moieties.
6. The compound of claim 1 wherein each R¹ and R² is independently chosen from H, $C_{1-10}$ alkyl, and $C_{2-10}$ alkenyl.
7. The compound of claim 1 wherein B is —CR³R⁴—.
8. A polymer comprising as polymerized units one or more compounds of claim 1.
9. A composition comprising one or more oligomers comprising as polymerized units one or more arylcyclobutene monomers, and one or more compounds of claim 1.
10. The composition of claim 9 further comprising one or more organic solvents.
11. The composition of claim 9 wherein the one or more arylcyclobutene oligomers has the formula

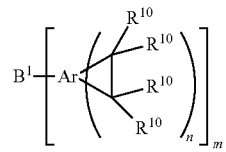

wherein B¹ is an n-valent linking group; Ar is a polyvalent aryl group and the carbon atoms of the cyclobutene ring are bonded to adjacent carbon atoms on the same aromatic ring of Ar; m is an integer of 1 or more; n is an integer of 1 or more; and each R¹⁰ is a monovalent group.
12. The composition of claim 9 further comprising one or more photoactive compounds.
13. A method of forming a film on a substrate comprising: providing a substrate; coating a layer of a composition of claim 9 on a surface of the substrate; and curing the coating.

* * * * *